US010579928B2

United States Patent
Wang et al.

(10) Patent No.: US 10,579,928 B2
(45) Date of Patent: Mar. 3, 2020

(54) LOG-BASED PREDICTIVE MAINTENANCE USING MULTIPLE-INSTANCE LEARNING

(71) Applicant: Siemens Aktiengesellschaft, Munich (DE)

(72) Inventors: Zhuang Wang, Wyncote, PA (US); Fabian Moerchen, Bainbridge Island, NJ (US); Dmitriy Fradkin, Princeton, NJ (US)

(73) Assignee: Siemens Aktiengesellschaft, Munich (DE)

( * ) Notice: Subject to any disclaimer, the term of this patent is extended or adjusted under 35 U.S.C. 154(b) by 548 days.

(21) Appl. No.: 14/427,677

(22) PCT Filed: Sep. 16, 2013

(86) PCT No.: PCT/US2013/059946
§ 371 (c)(1),
(2) Date: Mar. 12, 2015

(87) PCT Pub. No.: WO2014/043623
PCT Pub. Date: Mar. 20, 2014

(65) Prior Publication Data
US 2015/0227838 A1    Aug. 13, 2015

Related U.S. Application Data

(60) Provisional application No. 61/701,897, filed on Sep. 17, 2012.

(51) Int. Cl.
*G06N 5/04*      (2006.01)
*G06N 7/00*      (2006.01)
(Continued)

(52) U.S. Cl.
CPC ............. *G06N 5/04* (2013.01); *G06F 11/008* (2013.01); *G06N 7/00* (2013.01); *G06N 20/00* (2019.01); *G16H 40/40* (2018.01)

(58) Field of Classification Search
None
See application file for complete search history.

(56) References Cited

U.S. PATENT DOCUMENTS

| | | | |
|---|---|---|---|
| 2005/0172162 A1* | 8/2005 | Takahashi | G06F 11/0709 714/4.4 |
| 2006/0064415 A1 | 3/2006 | Guyon et al. | |
| 2011/0296244 A1* | 12/2011 | Fu | G06F 11/3608 714/37 |

OTHER PUBLICATIONS

Joseph F. Murray, et al. "Machine Learning Methods For Predicting Failures In Hard Drive: A Multiple-Instance Application". In Journal of Machine Learning Research, vol. 6, 2005 (pp. 783-816).

(Continued)

*Primary Examiner* — Li Wu Chang

(57) ABSTRACT

A method of building a model for predicting failure of a machine, including parsing (41) daily machine event logs of one or more machines to extract data for a plurality of features, parsing (42) service notifications for the one or more machine to extract failure information data, creating (43) bags from the daily machine event log data and failure information data for multiple instance learning by grouping daily event log data into the bags based on a predetermined predictive interval, labeling each bag with a with a known failure as positive, and bags without known failures as negative, where a bag is a set of feature vectors and an associated label, where each feature vector is an n-tuple of features, transforming (44) the multiple instance learning bags into a standard classification task form, selecting (45) a subset of features from the plurality of features, and training (46) a failure prediction model using the selected subset of features.

13 Claims, 7 Drawing Sheets

(51) Int. Cl.
*G06N 20/00* (2019.01)
*G06F 11/00* (2006.01)
*G16H 40/40* (2018.01)

(56) References Cited

OTHER PUBLICATIONS

Multiple-Instance Learning. from Wikipedia (1 Page).
Support Vector Machine. From Wikipedia. 12 Pages.
Regularization Perspectives On Support Vector Machines. From Wikipedia. 4 Pages.
Rong-En Fan, et al. "Liblinear: A Library For Large Linear Classification". In Journal of Machine Learning Research, vol. 9, 2008 (pp. 1871-1874).

* cited by examiner

| TimeStamp | EventCode | Message |
|---|---|---|
| 2010-09-08 20:10:51 | ABC 59 | ReconDone(IsvStatusSuccess) after 0 received images for ... |
| 2010-09-08 20:10:51 | ABC 49 | Timer was started waiting for ... |
| 2010-09-08 20:10:52 | ABD 46 | Receiving IsvMsgReconRequestDonemessage of size 80 Bytes from IRS. |
| 2010-09-08 20:10:52 | CDE 46 | Control info CDE (E c0 03 25 20 a2 00 00) |
| 2010-09-08 20:10:52 | XYZ 10 | SsqCtrl: Mode loading initiated: @PatientID@=... |
| 2010-09-08 20:10:52 | FGH 17 | SKIP button is hidden |
| 2010-09-08 20:10:53 | CDE 45 | IS ImagingSystemFinished received. |

| C | A | description |
|---|---|---|
| 16389 | 75552 | #instances |
| 3073 | 11238 | #features |
| 88 | 108 | #known failures |
| 6664 | 14367 | #bags |

FIG. 5

| | C | A |
|---|---|---|
| random | 0.037 (0.004) | 0.017 (0.003) |
| AllInst. | 0.293 (0.014) | 0.620 (0.013) |
| Agg. | 0.174 (0.013) | 0.498 (0.016) |
| MILES | 0.170 (0.011) | 0.427 (0.117) |
| MI-SVM | 0.216 (0.038) | 0.700 (0.014) |
| Ours | 0.319 (0.015) | 0.730 (0.011) |

FIG. 6

(a) Dataset C (b) Dataset A

|     | I    | II   | III  |
|-----|------|------|------|
| I   | 0.43 | 0.70 | 0.59 |
| II  | 0.45 | 0.87 | 0.70 |
| III | 0.32 | 0.77 | 0.71 |

LOG-BASED PREDICTIVE MAINTENANCE USING MULTIPLE-INSTANCE LEARNING

CROSS REFERENCE TO RELATED UNITED STATES APPLICATIONS

This application claims priority from "Log-Based Predictive Maintenance", U.S. Provisional Application No. 61/701,897 of Wang, et al., filed Sep. 17, 2012, the contents of which are herein incorporated by reference in their entirety.

TECHNICAL FIELD

This application is directed to methods for predictive maintenance for anticipating machine failures.

DISCUSSION OF THE RELATED ART

The success of a manufacturing company depends on the reliability of their products. Scheduled maintenance is widely used to ensure that machinery is operating correctly so as to avoid unexpected breakdowns. Such maintenance is often carried out for every component separately, based on its usage or on some fixed schedule. However, scheduled maintenance is labor-intensive and ineffective in identifying issues that develop between scheduled technician's visits. Unforeseen failures may still frequently occur. In contrast, predictive maintenance techniques can help determine the condition of in-service machinery to predict when and what repairs should be performed. The goal of predictive maintenance is to enable proactive scheduling of corrective work, and thus prevent unexpected machine failures, increasing machinery availability and improving customer service quality.

Predictive maintenance strives to anticipate machine failures to allow for advance scheduling of corrective maintenance, to prevent unexpected machine downtime and improving customer service quality. Predictive maintenance requires insight into the running condition of the machinery. This can be gained by adding sensors to the machine for recording and monitoring of signals of interest, such as temperature and voltage. A predictive maintenance module can then send alerts when sensor values deviate from normal ranges. Though sometimes an effective solution, it is impractical for in-service machine, since major hardware upgrades, such as adding sensors, are often infeasible, especially on large fleets, due to cost, effort and potential regulatory hurdles. Alternatively, one can gain insight into the workings of a machine by studying its logs. Modern machinery is usually operated via software applications. For example, in case of medical scanners, all device operations, from warming up to scanning a patient and from generating a medical report to calibration, are controlled by various software applications. These applications produce logs of their operation. These logs reflect the developers' original ideas about what are the valuable events to report, and contain informational or error messages, internal states, or exceptions. Theoretically, one can trace back how a machine was used by analyzing its logs. Mining such rich information can help to detect potential issues in advance.

The use of machine logs to predict failures poses challenges and has not yet been fully explored. Since logs are mainly used for debugging purposes, they (i) rarely contain explicit information for failure prediction; (ii) contain heterogeneous data including symbolic sequences, numeric time series, categorical variables and unstructured text; and (iii) can accumulate massive amounts of data, posing computational challenges. To make use of log data, one first interprets the logs, filters out noise, i.e. irrelevant data, and extracts predictive features. Next, one collects known failure cases for learning/evaluating models, transforms the task into an appropriate learning scenario and determines a performance measurement that reflects real-world needs. Then, one needs to apply advanced machine learning techniques based on multiple-instance learning to effectively and efficiently solve the learning task. Moreover, one should take into account specifics of the domain.

SUMMARY

Exemplary embodiments of the disclosure as described herein generally include systems and methods for a data-driven approach for predictive maintenance using logs. A data-driven approach according to embodiments of the disclosure are based on multiple-instance learning for predicting machine failures by mining machine event logs which, while usually not designed for predicting failures, contain rich operational information. Using historical daily log data from the instruments, embodiments build a model to capture patterns that can discriminate between normal and abnormal instrument performance for an interested component. The learned pattern is then used to predict the failure of the component by using the daily log data from an instrument. Methods according to embodiments of the disclosure were evaluated on two real-world medical device datasets, and the experiments show viability of a predictive maintenance approach according to an embodiment of the disclosure According to an aspect of the invention, there is provided a method of building a model for predicting failure of a machine, including parsing daily machine event logs of one or more machines to extract data for a plurality of features, parsing service notifications for the one or more machine to extract failure information data, creating bags from the daily machine event log data and failure information data for multiple instance learning by grouping daily event log data into the bags based on a predetermined predictive interval, labeling each bag with a with a known failure as positive, and bags without known failures as negative, where a bag is a set of feature vectors and an associated label, where each feature vector is an n-tuple of features, transforming the multiple instance learning bags into a standard classification task form, selecting a subset of features from the plurality of features, and training a failure prediction model using the selected subset of features.

According to a further aspect of the invention, features include event codes, event code variations, and numerical values associated with the event codes and event code variations.

According to a further aspect of the invention, transforming the multiple instance learning bags into a standard classification task from includes transforming each feature vector in a bag with a negative label into a negative example, and for each bag with a positive label, creating a meta-positive example by computing a mean of the feature vectors in the bag.

According to a further aspect of the invention, selecting a subset of features from the plurality of features includes creating multiple subsets by randomly subsampling negative bags and including all positive bags, learning a sparse linear classifier on each subset, and averaging weights from each sparse linear classifier and selecting features with the highest absolute weights.

According to a further aspect of the invention, training a failure prediction model using the selected subset of features includes learning the failure prediction model using the selected subset of features and all event log instances for the selected subset of features.

According to a further aspect of the invention, learning the failure prediction model includes finding a set of weights w that minimizes $$\frac{\lambda}{2}\|w\|_1^2 + \sum_j \max\{1 - y_j w^T x_j, 0\},$$

where $\lambda > 0$ is a user-specified regularization parameter, $y_j \in \{+1, -1\}$ is a label for bag j, and $x_j$ is a vector of the selected subset of features for bag j.

According to a further aspect of the invention, the method includes using the failure prediction model on new instances from the daily machine event log where an alert is triggered if a prediction value is greater than a predetermined threshold.

According to a further aspect of the invention, the method includes evaluating the failure prediction model by outputting a maximal prediction score of all instances in a bag.

According to another aspect of the invention, there is provided a computer-implemented method of building a model for predicting failure of a machine, including parsing daily machine event logs of one or more machines to extract data for a plurality of features, parsing service notifications for the one or more machine to extract failure information data, creating bags from the daily machine event log data and failure information data for multiple instance, where a bag is a set of feature vectors and an associated label, where each feature vector is an n-tuple of features, transforming the multiple instance learning bags into a standard classification task form by transforming each feature vector in a bag with a negative label into a negative example, and for each bag with a positive label, creating a meta-positive example by computing a mean of the feature vectors in the bag, selecting a subset of features from the plurality of features, and training a failure prediction model using the selected subset of features.

According to a further aspect of the invention, creating bags from the daily machine event log data and failure information data for multiple instance learning includes grouping daily event log data into the bags based on a predetermined predictive interval, labeling each bag with a with a known failure as positive, and bags without known failures as negative.

According to a further aspect of the invention, selecting a subset of features from the plurality of features includes creating multiple subsets by randomly subsampling negative bags and including all positive bags, learning a sparse linear classifier on each subset, and averaging weights from each sparse linear classifier and selecting features with the highest absolute weights.

According to a further aspect of the invention, training a failure prediction model using the selected subset of features includes learning the failure prediction model using the selected subset of features and all event log instances for the selected subset of features by finding a set of weights w that minimizes $$\frac{\lambda}{2}\|w\|_1^2 + \sum_j \max\{1 - y_j w^T x_j, 0\},$$

where $\lambda > 0$ is a user-specified regularization parameter, $y_j \in \{+1, -1\}$ is a label for bag j, and $x_j$ is a vector of the selected subset of features for bag j.

According to another aspect of the invention, there is provided a non-transitory program storage device readable by a computer, tangibly embodying a program of instructions executed by the computer to perform the method steps for of building a model for predicting failure of a machine.

BRIEF DESCRIPTION OF THE DRAWINGS

FIG. 5 is a table that summarizes datasets used for testing, according to embodiments of the disclosure.

FIG. 6 is a table of PM-AUC comparisons, according to embodiments of the disclosure.

DETAILED DESCRIPTION OF EXEMPLARY EMBODIMENTS

Figure 1:
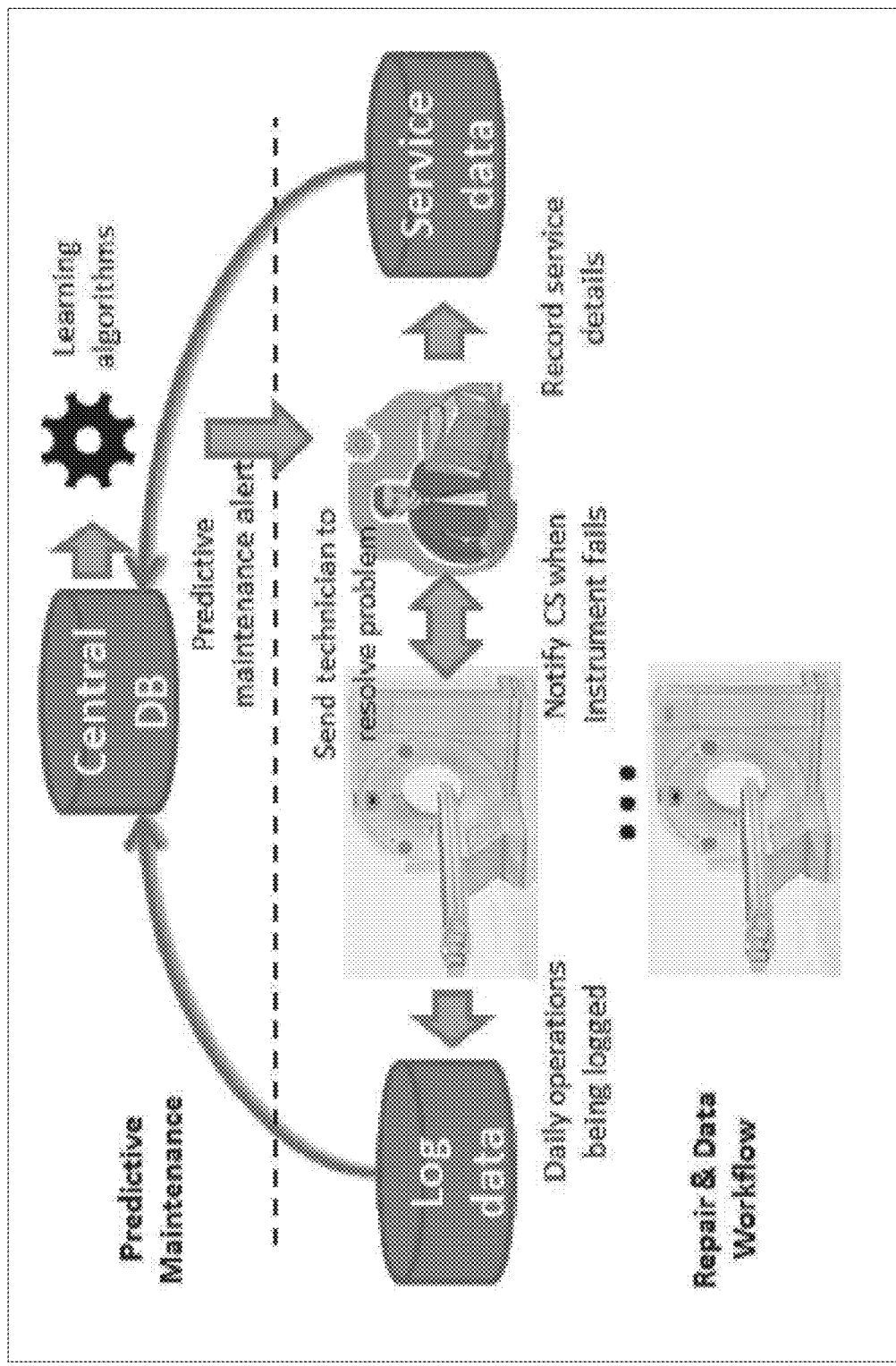
FIG. 1. illustrates a predictive maintenance workflow, according to embodiments of the disclosure.

Exemplary embodiments of the disclosure as described herein generally provide systems and methods for a data-driven approach for predictive maintenance using logs. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Data Description

A typical service life cycle is as follows: machinery operates normally at first. When unexpected or undesirable behavior occurs, the customer calls the service center for support, a "notification" is opened and repair service is scheduled. Then a technician comes on-site to resolve the issue. After it is resolved, the technician updates the notification with the repair details such as component consumption information, hours spent, trouble-shooting or repair description, and closes the notification. Throughout the process, during both normal and abnormal operation, the machine automatically records all events into log files. This cycle, illustrated in the bottom part of FIG. 1, is repeated over and over in a fleet of thousands of medical machine units. The log files from such a fleet collected over the past several years form the data for this disclosure. Although data from medical devices was used to demonstrate an approach according to an embodiment of the disclosure, it is to be understood that an approach according to an embodiment of the disclosure is applicable to other domains, such as IT infrastructure or any industrial machinery in which machine logs are recorded.

Figures 2, 3:
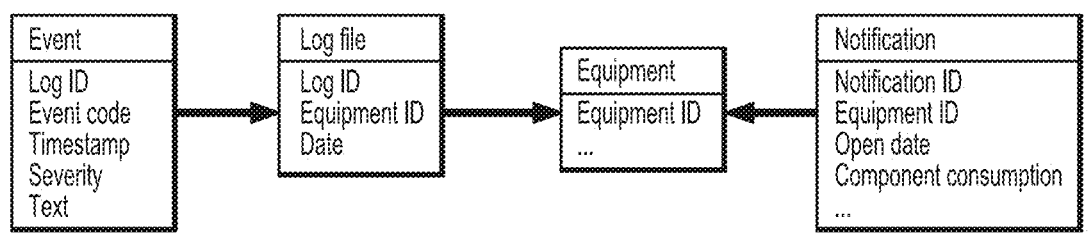
FIG. 2 illustrates a portion of a real log file from a medical scanner, according to embodiments of the disclosure.
FIG. 3 illustrates a generic event-response diagram for predictive maintenance that shows logical relationships between entities in predictive maintenance domains, according to embodiments of the disclosure.

There are two types of data: log data and service data. Log data is a collection of events recorded by various applications running on the machinery. FIG. 2 illustrates a portion of a real log file, with renamed event codes and messages, from a medical scanner, and FIG. 3 illustrates a generic event record diagram for predictive maintenance that shows logical relationships between entities in predictive maintenance domains. An event includes a timestamp that indicates when the event occurred, a message text that may be fully unstructured or generated from a template that describes the event, an event code that represents the category of a group of similar message text, and an event severity. Events reflect the developers' original idea about what are the valuable states to report. According to embodiments of the disclosure, there are thousands of unique event codes and a theoretically unlimited number of distinct messages texts. An machine log is usually broken into day-long pieces. A daily log can contain tens of thousands of events since the time resolution of events can be as small as a few seconds.

Log data is unique in several aspects. It is temporal, and can be viewed both as symbolic sequences (over event codes) and as numeric time series, with variables extracted from messages or with event frequencies over some window, such as days. In addition, it can include categorical features, such as event codes, and categorical variables in text, and fully unstructured data such as message text. Some text similarity between message text may make sense, in particular in the absence of event code categories.

An experienced domain expert can scan machine logs to identify abnormal conditions. The old-fashioned predictive maintenance approach is to manually create predictive patterns for a particular component based on the boolean combination of a few relevant event codes. Such an approach is heavily experience-based and very time consuming, but illustrates an important concept: that component failure can be predicted by checking daily logs for patterns that include multiple event codes.

Service data is another data type in predictive maintenance applications. Service notifications or tickets are used by a service center to record details of performed services such as the notification open date (i.e. the date a customer reports a malfunction), the machine involved, the component consumption, etc. Under a reasonable, though not always correct, assumption that component replacement is the consequence of a failure of that particular component, this information can be used to correlate a known component failure with its corresponding machine, time and relevant logs.

However, service data is noisy and often includes incorrect information. A replacement of a component might be ordered but not used and later sent back to the factory; or a component may be exchanged but the repair may not have been appropriate for the malfunction at hand. In addition, some failure modes do not involve component exchanges and need to be identified by matching certain keywords in the notification text, such as "greasing" or "recalibrating".

Given a target component and a collection of historical machine log and service data, a predictive maintenance task can be formulated for the target component by constructing a binary classifier for predicting failures, where training examples contain predictive features extracted from an interval of machine's log, and the label is determined by the occurrence of the component replacement in the service data after that interval. Note that anr approach according to an embodiment of the disclosure is not specific to certain failure types, but targets all hardware failures within business needs that can be rectified by replacing or repairing the failing component and can be detected via logged data caused by aberrant or inoperable behavior.

Predictive Maintenance Workflow

An exemplary predictive maintenance workflow according to an embodiment of the disclosure is illustrated in the top part of FIG. 1. A central database is at the core of a predictive maintenance platform, in which data from in-service machinery and the support centers is collected and integrated. An analytic module processes data from the central database. Analysis includes data preparation, model building, model evaluation, and monitoring. To build a model for a target component, the analytic module first pulls the relevant data from the central database, extracts predictive features (see below), and transforms and represents the data in a matrix format for learning algorithms. Learning algorithms can build models and then pass them on for evaluation. A model is evaluated against historical data and scored by several key performance indicators. After evaluation, domain experts can review the model's performance and decide whether to deploy the model into the system. In the monitoring module, the system pulls the new daily log data from monitored machine to predict whether a component will fail using a model. If a predicted score exceeds a predefined threshold, an alert will be sent to the service center for further review.

Requirements

Domain experts were consulted to determine requirements that would make a log-based predictive maintenance solution practical and useful. These requirements, summarized below, served as a guideline for an approach according to an embodiment of the disclosure.

The timing of an alert is useful for the evaluation of the quality of a model in predictive maintenance. Embodiments of the disclosure make the following definitions:

Predictive Interval: a pre-defined time interval right before a failure. An alert occurring in this interval gives enough time for the support center to act and is considered successful.

Infected Interval: a pre-defined time interval right after a failure. The machine is breaking down or under repair. Data from this interval should not be used for modeling/evaluation.

Responsive Duration: a pre-defined time length reflecting real-life action time for an alert.

True and false positives are then defined as:

True Positive: an alert that occurs in the predictive interval. Note that multiple alerts in the same predictive interval only count as one true positive.

False Positive: an alert that occurs outside the predictive/infected interval. Note that multiple such alerts within a responsive duration only count as one false positive.

Finally, using the definitions above, one can evaluate the performance of a model using precision and recall:

Precision: True Positive/(True Positive+False Positive).

Recall: True Positive/All failures.

The maintenance strategy is determined separately for different components and is influenced by many factors, such as repair cost, failure severity and the business model. Learning algorithms should balance between precision and recall and provide flexibility in trading these off. Without knowledge of a specific maintenance strategy, a model with a Predictive-Maintenance-based Area Under precision-recall Curve (PM-AUC) score can be evaluated as a simple measurement. PM-AUC is computed like a regular AUC but using the above definitions of recall and precision.

Other requirements are not formally defined, but are present nonetheless, so will be briefly discussed.

Interpretability: A model should be interpretable so that experts may review it. This allows for incorporation of expert feedback into the modeling process. Embodiments of the disclosure use linear classification with L1 regularization to build a sparse linear model which the domain experts can easily review. Such a model includes a weighted sum of a relatively small numbers of predictive features, with the weights specifying their precise contributions to the decision. Furthermore, known noisy or irrelevant features specified by experts can be easily excluded from a modeling process according to embodiments of the disclosure. In some cases just knowing that the model is "interpretable" and understanding which features affect model performance can make experts more comfortable in adopting it.

Efficiency: A learning algorithm according to embodiments of the disclosure should be fast and capable of handling hundreds of thousands of training examples in a space of tens of thousands features. Embodiments of the disclosure use state-of-the-art sparse linear classifiers to achieve this. An exemplary, non-limiting example is the Liblinear package.

Handling Class Imbalance: The number of known failures is usually small. It should be possible to learn models with only tens of known failure cases. To deal with such extremely imbalanced labeled data, embodiments apply a combination of stratified sampling, stable feature selection and large margin techniques to prevent overfitting and to learn a robust model.

Methodology

The task of building a learning model for predictive maintenance may be viewed as an example of Multi-Instance Learning (MIL). In MIL, instead of receiving a set of independent labeled instances as in standard classification, the learner receives a set of bags which are labeled positive or negative. Each bag may contain multiple instances. A bag is labeled negative if all the instances in it are negative, and positive if it contains at least one positive. The goal is to build a classifier that will label either unseen bags or unseen instances correctly. Embodiments of the disclosure may treat the machine daily logs as instances, all the logs from the surrounding interval (e.g. within a week) as a bag of instances and the bag label as a failure or non-failure depending on the service notifications. Given a number of bags obtained from numerous machines and at different dates, the task of failure prediction may be treated as MIL. In this task, unseen bags are labeled and the accuracy of models is measured at the bag level.

An MIL formulation according to an embodiment of the disclosure captures several important aspects of the task:

It is more realistic to assume that at least one daily log within a short interval before a failure carries a failure signature than to assume that all the daily logs within a short interval before a failure to carry a failure signature, because it is more common for machines to continue working irregularly, switching between normal and abnormal conditions, before a final breakdown. The fact that all the daily logs are normal within a non-failure interval is well captured.

An MIL objective according to an embodiment of the disclosure is to correctly label a bag rather than every instance. This is strictly consistent with the domain-based evaluation metric. More specifically, a positive bag which is correctly classified corresponds to a domain-based true positive and a negative bag which is incorrectly classified corresponds to a domain-based false positive.

Embodiments of the disclosure may formally define the learning task as follows. Let D be a set of B labeled bags, $D=\{bag_j; j=1, \ldots, B\}$, where $bag_j=(\{x_{ij}; i=1, \ldots, b_j\}, y_j)$, $x_{ij} \in \mathbb{R}^d$ is a feature vector of the i-th instance from the j-th bag, $y_j \in \{+1, -1\}$ is the binary label of the j-th bag and $b_j$ is the number of instances in the j-th bag. An objective according to embodiments of the disclosure is to learn a model f whose decision function sgn(f(bag)) accurately predicts the label of a bag.

A challenge in a task domain according to an embodiment of the disclosure comes from the label imbalance and the low quality of positive labels. Since labeling is based on service notifications, which are not entirely reliable, even slightly inaccurate notification dates would change the identification of positive bags, if this is not taken into account. Moreover, as the known failure cases are rare, any noisy positive bags would downgrade the model quality. Recent advances in MIL have resulted in many successful algorithms for learning f, but most of these models are not robust to label noise in situations with imbalanced data. A simple algorithm according to an embodiment of the disclosure which is robust to label noise for the rare class is described as follows.

According to an embodiment of the disclosure, the MIL dataset is transformed as follows: if the j-th bag is negative, create multiple negative instances $(x_{ij}, -1)$ by an instance-to-example approach, because all instances in negative bags are part of normal operation and are not indicative of failure. If the j-th bag is positive, create positive examples by averaging all its instances into a single positive meta example $(x_j, +1)$, where $x_j=mean(\{x_{ij}\}, i=1, \ldots, b_j)$. One rationale for this is that the new meta-example is guaranteed to be positive since there is at least one positive instance in the bag. Although it compromises some level of the discriminative power of positive examples due to features from negative instances, the averaging strategy improves the label quality of positive examples which is more critical for imbalanced data.

Joining all the newly created examples from all the bags into a single training dataset $D'=\{(x_j, y_j), j=1, \ldots, M\}$, embodiments of the disclosure formulate the learning task as an L1-regularized SVM optimization, $\min_w$ $$\frac{\lambda}{2}\|w\|_1^2 + \sum_j \max\{1 - y_j w^T x_j, 0\},$$

where $\lambda>0$ is a user-specified regularization parameter. The optimization can be efficiently solved by a state-of-the-art SVM solver, such as Liblinear. To predict the label of a bag in the evaluation process, embodiments use the maximal prediction score of all the instances in the bag, $f(bag_j)=\max(\{w^T x_{ij}\}, i=1, \ldots, b_j)$.

Once a model according to an embodiment of the disclosure has been learned and is ready to be used in a real-life deployment scenario, the MIL approach may be abandoned—the learned model may be applied to individual instances, not to the bags. Note that if bags are formed, using the maximum score over instances as the score for the bag would results in earliest alerts being triggered on the same days. In other words, a prediction is generated separately for each daily log, and an alert is triggered if the prediction score exceeds a pre-defined threshold.

Feature Representation: Embodiments of the disclosure may use a bag-of-word-based method to extract predictive information from daily logs. Several entities may be extracted from logs as "words" as summarized below:

Keywords: Bag-of-keyword is a fine-grained feature representation which can easily blow up the feature space to millions of dimensions. Since it poses computational and interpretive challenges n the final model, embodiments do not use keywords.

Numerical values: Numerical values are often used to record important physical or mechanical conditions. Extracting such values from text is a highly domain-dependent task because the values are often encoded to hide sensitive information. Given the high cost of domain effort for decoding, embodiments may extract a limited number of numerical values and represent each with several statistic-based features.

Event codes: An event code is a developer-specified category of a group of similar message texts. It is a high-level summary of the event content. Since event codes are domain-friendly, as they are widely used in traditional pattern creation processes, and the extraction is fully domain-independent, embodiments may use them as basic features.

Event code variations: Textually similar messages from the same event code might be logically different. For example, "the scanning button is on" and "the scanning button is off" come from the same event code but record two totally different operations. To separate these logically different messages from the same event code, event codes may be decomposed into event code variations. For all message texts from the same event code, embedded numerical values are filtered out and then each distinct message template is identified as a new event code variation. This type of feature is highly desirable by domain experts.

Sequences: Sequential features capture the logical order of events and enhance the interpretability of a final model according to an embodiment of the disclosure. Experiments have been conducted with event-code-based sequence features generated by a novel sequential pattern-mining algorithm designed for MIL.

Feature Selection: Embodiments of the disclosure may use a bootstrapped feature selection algorithm to select a subset of relevant features for building robust learning models with imbalanced labels. Stable feature selection may be performed by training multiple sparse linear classifiers under stratified subsampling. Embodiments may create each sample of data by including all positive bags and a set of randomly selected negative bags. A sparse linear classifier is trained on the sample to learn the model weights $w_i$, where i is the index of a feature. After repeating this process multiple times, one may calculate $|\Sigma_i w_i|$, rank features by these values and then select the features by retaining only those with the highest rankings. Afterwards, the selected features are used for another sparse linear classification on all the training data to learn the final model.

Figure 4:
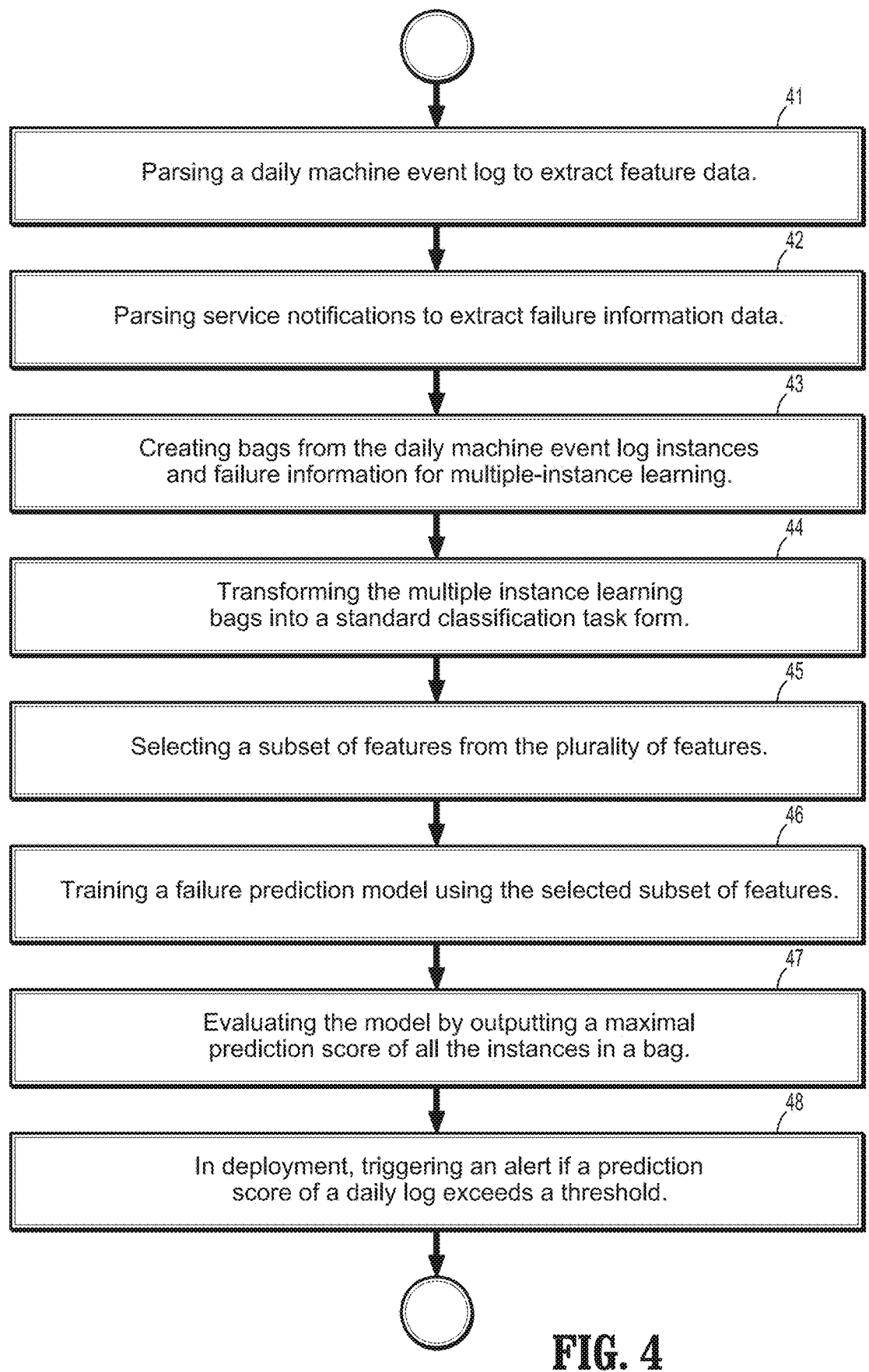
FIG. 4 is a flowchart of a predictive maintenance algorithm, according to embodiments of the disclosure.

An approach according to an embodiment of the disclosure is summarized below, with reference to the steps of the flowchart in FIG. 4.

Learning:
1. Parse daily event logs to extract data for a plurality of features (step 41).

2. Parse service notifications to extract known failure information data (step 42).
3. Create bags for MIL learning (step 43).
 (a) Group daily event log data into bags using desired interval lengths.
 (b) Label bags with known failures as positive and the rest as negative.
4. Transform the MIL bags into a standard classification task form(step 44).
 (a) Each instance in a negative bag is transformed into a negative example.
 (b) For each positive bag, create a meta-positive example using the mean of bag's feature vector data instances.
5. Feature selection (step 45).
 (a) Create multiple subsets by randomly subsampling negative bags and including all positive bags.
 (b) Learn a sparse linear classifier on each subset.
 (c) Average weights from each classifier and select those features with the highest absolute weights.
6. Train the final model (step 46).
 (a) Use the subset of features obtained in the previous step.
 (b) Learn the final model by using all the data.

Prediction:
1. In evaluation, output the maximal prediction score of all the instances in a bag (step 47).
2. In deployment, trigger an alert if the prediction score of a daily log hits the pre-defined threshold (step 48).

Experiments

Data for testing embodiments of the disclosure has been collected over the last several years from two large fleets of medical machines from a major medical device provider. For each type of machine, a target component of high practical interest is chosen with a sufficient number of known failure cases. An exemplary, non-limiting value for the Predictive Interval is 7 days, for the Infected Internal is 20 days, and for the Responsive Duration is 7 days, for both predictive maintenance tasks. These values were agreed upon by domain experts, and no significant performance differences resulted from slightly changing the bag sizes. For each data set positive bags were created from the daily logs of the [−7 day, −1 day] interval before each failure, where day 0 is the notification open date, and negative bags by randomly selecting about 20% of all the remaining weekly intervals. The resulting datasets A and C from two different fleets of medical machinery with different targeted components are summarized in FIG. 5.

Domain-based Evaluation: An algorithm according to an embodiment of the disclosure may be evaluated by comparing it against the following methods using the domain-based metrics discussed in the requirements section, above:

AllInstances: A baseline wrapper algorithm that transforms MIL into standard supervised learning by assigning the bag label to its instances.

Aggregated: Another baseline wrapper algorithm that transforms MIL into standard supervised learning by aggregating each bag into a meta-example through averaging.

MILES: A popular MIL wrapper algorithm that transforms MIL into standard supervised learning by embedding each bag into a new feature space defined by distances to training instances.

MI-SVM: An iterative algorithm that solves the optimization formulation of MIL as a maximum margin task.

The PM-AUC scores of these methods are shown in the table of FIG. 6. For the wrapper algorithms, the L1-regularized Linear SVM with the bootstrapped feature selection is used for supervised learning. Experimental results (mean and standard deviation) are reported based on bag-level 5-fold cross validation with stratified sampling for imbalanced positive labels. All hyper-parameters were selected using validation. These results show that an approach according to an embodiment of the disclosure outperforms other methods in terms of the PM-AUC.

Figure 7:
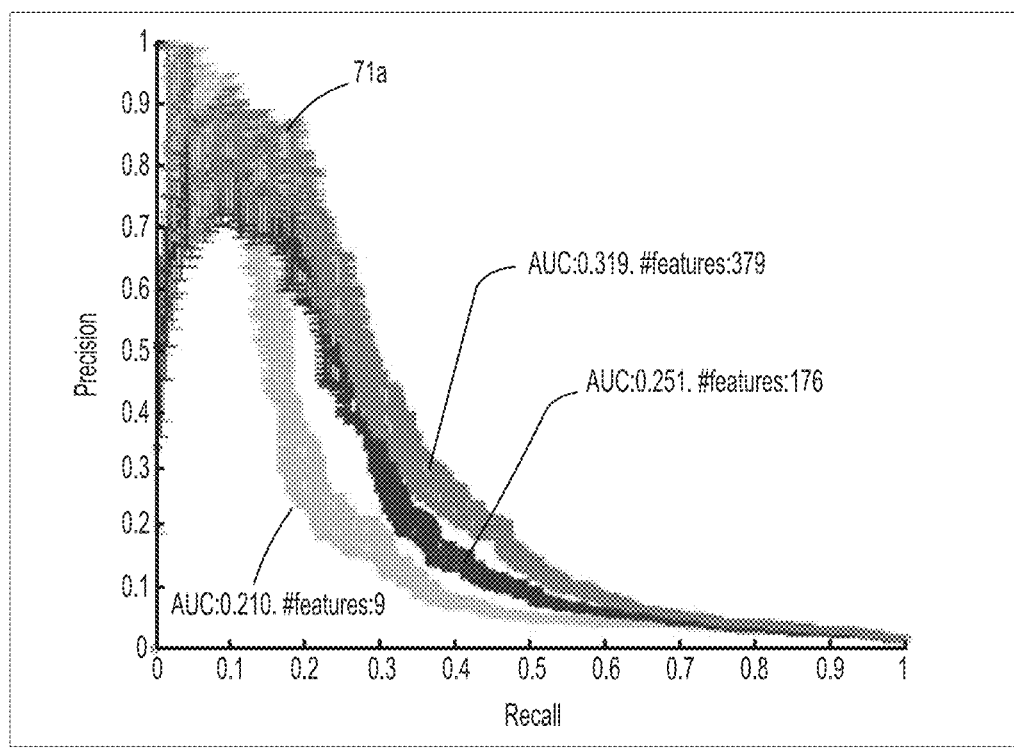
FIGS. 7(a)-(b) depicts PM-ROC curves for different datasets for models with different complexity learned by an algorithm according to an embodiment of the disclosure.
Figure 7:
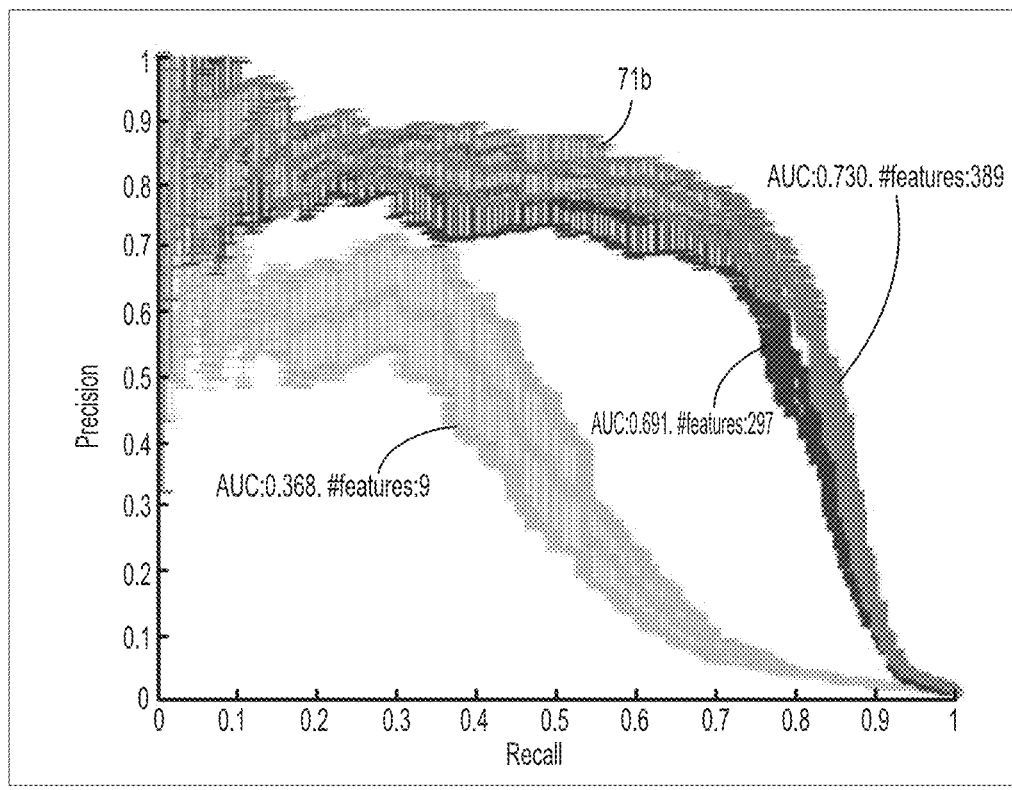

A maintenance strategy is determined by business units separately for different machine or components, which is why predictive models have to allow for trade-offs between precision and recall according to the specific strategy. FIGS. 7(a)-(b) depicts the PM-ROC curves for datasets A and C, respectively, showing the mean and 90% confidence interval from 5-fold cross validation of the models with different complexity, controlled by adjusting the L-1 regularization parameter, learned by an algorithm according to an embodiment of the disclosure. In both figures, one can observe that the curves 71a and 71b, representing models composed of 300 to 400 predictive features, achieve the best performance. If the business requirements are for 70% precision, then models according to embodiments of the disclosure can cover 25% and 80% of failures within the 7-day Predictive Interval for each dataset, respectively. Simpler models, with fewer features, may be desirable from both the machine learning and the domain points of view. Though the most complicated models, with 300 to 400 features, achieve the best PM-AUC scores on both datasets, simpler models with less than ten features and suboptimal scores may still be useful. Their simplicity, together with relatively high precision and reasonable recall, enable domain experts to understand them and thus help detect root causes of failures and identify specific failure modes.

Figures 8, 9:
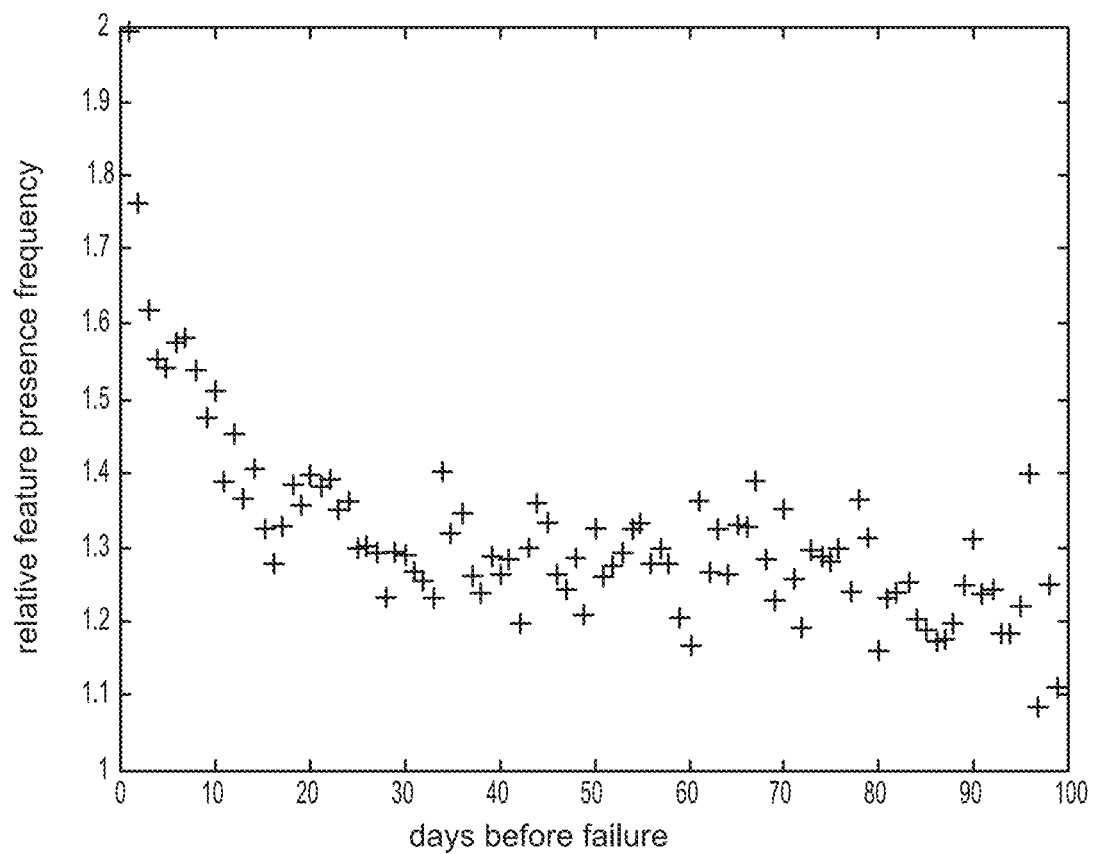
FIG. 8 is a plot of a fleet average relative frequency of one strongly positive feature vs. time to failure, according to embodiments of the disclosure.
FIG. 9 is a table of PM-AUC results of cross-testing of family-specific models, according to embodiments of the disclosure.

On Utility of Single Features: An interesting question is whether the effects of an impending failure can be observed over time by looking at only a few features. Experiments of embodiments of the disclosure suggest that while the frequencies of some features are in aggregate correlated with approaching failures, they are not strong predictors of failures in individual instances. For example, a plot of a fleet average relative frequency of a highly positive feature vs. the time to a failure is shown in FIG. 8. There is a clear upward trend close to the failure date. However, it should be kept in mind that this plot is an aggregate over multiple machines. It turns out that many positive instances do not contain this feature due to sparsity, and the value usually does not change smoothly or in the same direction between consequent days on the same machine. This could be an artifact of how the machine logs events or it could be related to utilization, which varies across days. In either case, additional knowledge to correct for these factors is lacking. Thus this feature alone is inadequate for failure prediction. This example illustrates why simple handcrafted rules utilizing only a handful of features do not work well, while machine learning approaches that can use even weak signals result in decent performance.

Global vs Local Models: Some types of machines may be setup differently due to specific customer needs, such as large and complex machinery that may be set up differently for different room layouts. The machines with the same setup belong to the same family. Do the machine logs from different families behave differently? Is the model learned from one family valid for the other ones?

To explore similarities between families, hierarchical clustering was performed on the machine daily bag-of-events features and some families were found to behave more similarly to each other than the others. By labeling the same features with their family types and feeding them into a multi-class classifier, one can correctly predict the family of a daily log with more than 80% accuracy on dataset A, which has 28 families. This indicates that there are noticeable differences between families. To explore the predictability of family-specific models on other families, an experiment was conducted by training a "local" classifier on each family and testing on the others. The results, in terms of PM-AUCs, of this experiment on the three largest families of dataset A are summarized in FIG. 9, where the score on the coordinate (I, II) corresponds to the model that is trained on the data from family I and tested on the data from family II. Most of the family-specific models achieve comparable scores in the cross-testing. The fact that the family-specific predictive power is transferable and that known failure cases are very rare suggests that training a global predictive model on data from all the families make sense in this task domain.

An approach according to an embodiment of the disclosure is currently used to monitor several fleets of medical machinery around the world. It was implemented and deployed on an SAS platform of a medical machine provider. The workflows were built with SAS Enterprise Miner to automate the process of model building and evaluation. Since SAS Enterprise Miner does not include L1-regularized classifiers for feature selection, an algorithm according to an embodiment of the disclosure was executed in a development environment to pre-select the features which provide the highest PM-AUC score. Only the selected features, usually a few hundred, are used in the SAS Enterprise Miner workflows. Based on the model performance on the held-out historical data, an alert threshold is selected to balance Precision and Recall according to business requirement for a target component. Once deployed, the workflows are regularly run on the machine logs which are pre-processed by SAS procedures and stored in the SAS data storage system. When a potential malfunction is identified, an alert is sent to the user. These alerts are reviewed by domain experts to determine the next steps. The system was deployed in early 2012 and has not been retrained to allow a long term real-life performance evaluation, although it makes sense to retrain the models periodically with the new data.

A real-world evaluation proceeds as follows: no corrective action is taken after receiving an alert during the evaluation period. After that, true positives, false positives and total failures are determined by the component replacement information from the Service Center. A workflow according to an embodiment of the disclosure for predicting a key medical scanner component failure was evaluated over several months on a subset of one fleet of several hundred scanners. The performance was similar to that on the experimental Dataset C: it successfully predicted 12 out of 31 failures within 1 week predictive interval and generated few (between 0 and 5) false alarms.

System Implementations

It is to be understood that embodiments of the present disclosure can be implemented in various forms of hardware, software, firmware, special purpose processes, or a combination thereof. In one embodiment, the present disclosure can be implemented in software as an application program tangible embodied on a computer readable program storage device. The application program can be uploaded to, and executed by, a machine comprising any suitable architecture.

Figure 10:
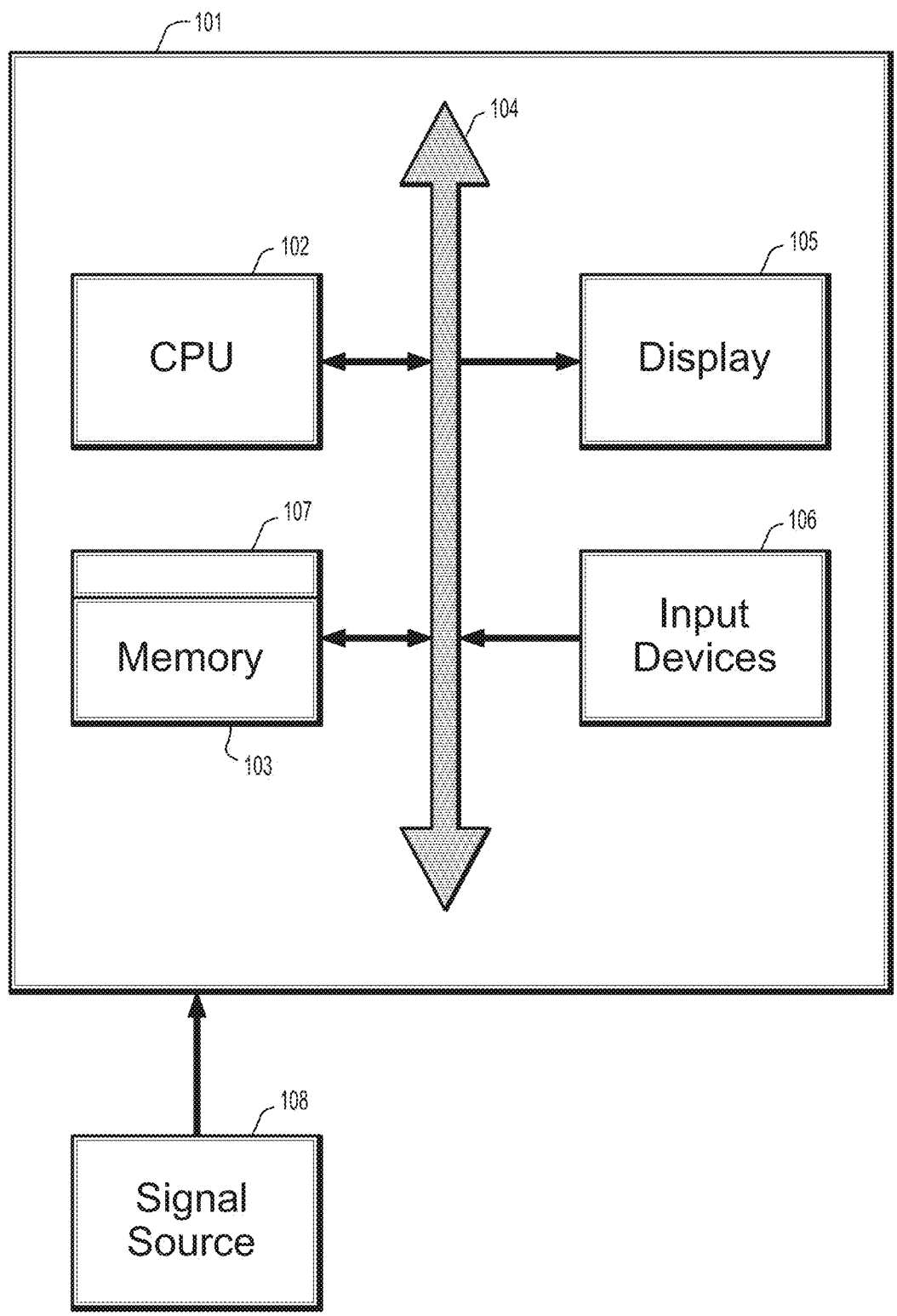
FIG. 10 is a block diagram of a system for implementing a data-driven approach for predictive maintenance using logs, according to an embodiment of the disclosure.

FIG. 10 is a block diagram of an exemplary computer system for implementing a data-driven approach for predictive maintenance using logs according to an embodiment of the disclosure. Referring now to FIG. 10, a computer system 101 for implementing the present disclosure can comprise, inter alia, a central processing unit (CPU) 102, a memory 103 and an input/output (I/O) interface 104. The computer system 101 is generally coupled through the I/O interface 104 to a display 105 and various input devices 106 such as a mouse and a keyboard. The support circuits can include circuits such as cache, power supplies, clock circuits, and a communication bus. The memory 103 can include random access memory (RAM), read only memory (ROM), disk drive, tape drive, etc., or a combinations thereof. Embodiments of the present disclosure can be implemented as a routine 107 that is stored in memory 103 and executed by the CPU 102 to process the signal from the signal source 108. As such, the computer system 101 is a general purpose computer system that becomes a specific purpose computer system when executing the routine 107 of the present disclosure.

The computer system 101 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present disclosure is programmed. Given the teachings of the present disclosure provided herein, one of ordinary skill in the related art will be able to contemplate these and similar implementations or configurations of the present disclosure.

While the present disclosure has been described in detail with reference to exemplary embodiments, those skilled in the art will appreciate that various modifications and substitutions can be made thereto without departing from the spirit and scope of the disclosure as set forth in the appended claims.

The invention claimed is:

1. A computer-implemented method of building a model for predicting failure of a machine, the method comprising the steps of:
parsing daily machine event logs of one or more machines to extract data for a plurality of features, the features associated with predicting machine failure;
parsing service notifications for the one or more machine to extract failure information data;
creating bags from the daily machine event log data and failure information data for multiple instance learning by grouping daily event log data into the bags based on a predetermined predictive interval, assigning a positive label to each bag with a known failure, and assigning a negative label to each bag having no known failures, wherein each bag comprises a respective set of feature vectors and an associated label, and wherein each feature vector is an n-tuple of features;
transforming each feature vector in a bag with a negative label into a corresponding negative example, and for each bag with a positive label, creating a respective meta-positive example by computing a respective mean of the feature vectors in each bag with a positive label;
selecting a subset of features from the plurality of features, wherein the subset of features defines a function for a failure prediction model to predict a bag label, and the selecting comprises:
creating multiple candidate subsets of features, wherein each candidate subset of features comprises features from all bags assigned the positive label and a random subsampling of features from bags assigned the negative label,
learning a sparse linear classifier on each candidate subset of features, wherein learning the sparse linear classifier on each candidate subset of features comprises learning a respective set of weights for each candidate subset of features; and
averaging the respective set of weights learned for each candidate subset of features and selecting features with the highest absolute weights as the subset of features;
training the failure prediction model using the selected subset of features; and
using the failure prediction model in deployment to monitor new instances of daily machine event logs wherein a prediction failure alert is triggered in response to receiving a failure prediction score that exceeds a predefined threshold.

2. The method of claim 1, wherein features include event codes, event code variations, and numerical values associated with the event codes and event code variations.

3. The method of claim 1, wherein training the failure prediction model using the selected subset of features comprises learning the failure prediction model using the selected subset of features and all event log instances for the selected subset of features.

4. The method of claim 3, wherein learning the failure prediction model comprises finding a set of weights w that minimizes $$\frac{\lambda}{2}\|w\|_1^2 + \sum_j \max\{1 - y_j w^T x_j, 0\},$$

wherein $\lambda > 0$ is a user-specified regularization parameter, $y_j \in \{+1, -1\}$ is a label for bag j, and $x_j$ is a vector of the selected subset of features for bag j.

5. The method of claim 1, further comprising:
evaluating a label prediction of a current bag by the trained failure prediction model using a maximal prediction score of all instances in the current bag.

6. A computer-implemented method of building a model for predicting failure of a machine, the method comprising the steps of:
parsing daily machine event logs of one or more machines to extract data for a plurality of features;
parsing service notifications for the one or more machine to extract failure information data;
creating bags from the daily machine event log data and failure information data for multiple instance learning, wherein each bag comprises a respective set of feature vectors and an associated label, wherein the associated label is a positive label or a negative label, and wherein each feature vector is an n-tuple of features;
transforming the multiple instance learning bags into a standard classification task form by transforming each feature vector in a bag with a negative label into a corresponding negative example, and for each bag with a positive label, creating a respective meta-positive example by computing a respective mean of the feature vectors in each bag with a positive label;

selecting a subset of features from the plurality of features, wherein the subset of features defines a function for a failure prediction model to predict a bag label, and the selecting comprises:

creating multiple candidate subsets of features, wherein each candidate subset of features comprises features from all bags assigned the positive label and a random subsampling of features from bags assigned the negative label, learning a sparse linear classifier on each candidate subset of features, wherein learning the sparse linear classifier on each candidate subset of features comprises learning a respective set of weights for each candidate subset of features, and averaging the respective set of weights learned for each candidate subset of features and selecting features with the highest absolute weights as the subset of features; and training the failure prediction model using the selected subset of features; and using the failure prediction model in deployment to monitor new instances of daily machine event logs wherein a prediction failure alert is triggered in response to receiving a failure prediction score that exceeds a predefined threshold.

7. The method of claim 6, wherein creating bags from the daily machine event log data and failure information data for multiple instance learning comprises grouping daily event log data into the bags based on a predetermined predictive interval, labeling each bag with a known failure as positive, and labeling bags without known failures as negative.

8. The method of claim 6, wherein training a failure prediction model using the selected subset of features comprises learning the failure prediction model using the selected subset of features and all event log instances for the selected subset of features by finding a set of weights w that minimizes $$\frac{\lambda}{2}\|w\|_1^2 + \sum_j \max\{1 - y_j w^T x_j, 0\},$$

wherein $\lambda > 0$ is a user-specified regularization parameter, $y_j \in \{+1, -1\}$ is a label for bag j, and $x_j$ is a vector of the selected subset of features for bag j.

9. A non-transitory program storage device readable by a computer, tangibly embodying a program of instructions executed by the computer to perform the method steps for building a model for predicting failure of a machine, the method comprising the steps of:

parsing daily machine event logs of one or more machines to extract data for a plurality of features, the features associated with predicting machine failure;

parsing service notifications for the one or more machine to extract failure information data;

creating bags from the daily machine event log data and failure information data for multiple instance learning by grouping daily event log data into the bags based on a predetermined predictive interval, assigning a positive label to each bag with a known failure, and assigning a negative label to each bag having no known failures, wherein each bag comprises a respective set of feature vectors and an associated label, and wherein each feature vector is an n-tuple of features;

transforming each feature vector in a bag with a negative label into a corresponding negative example, and for each bag with a positive label, creating a respective meta-positive example by computing a respective mean of the feature vectors in each bag with a positive label;

selecting a subset of features from the plurality of features, wherein the subset of features defines a function for a failure prediction model to predict a bag label, and the selecting comprises, creating multiple candidate subsets of features, wherein each candidate subset of features comprises features from all bags assigned the positive label and a random subsampling of features from bags assigned the negative label, learning a sparse linear classifier on each candidate subset of features, wherein learning the sparse linear classifier on each candidate subset of features comprises learning a respective set of weights for each candidate subset of features, and averaging the respective set of weights learned for each candidate subset of features and selecting features with the highest absolute weights as the subset of features;

training the failure prediction model using the selected subset of features; and using the failure prediction model in deployment to monitor new instances of daily machine event logs wherein a prediction failure alert is triggered in response to receiving a failure prediction score that exceeds a predefined threshold.

10. The computer readable program storage device of claim 9, wherein features include event codes, event code variations, and numerical values associated with the event codes and event code variations.

11. The computer readable program storage device of claim 9, wherein training flail the failure prediction model using the selected subset of features comprises learning the failure prediction model using the selected subset of features and all event log instances for the selected subset of features.

12. The computer readable program storage device of claim 11, wherein learning the failure prediction model comprises finding a set of weights w that minimizes $$\frac{\lambda}{2}\|w\|_1^2 + \sum_j \max\{1 - y_j w^T x_j, 0\},$$

wherein $\lambda > 0$ is a user-specified regularization parameter, $y_j \in \{+1, -1\}$ is a label for bag j, and $x_j$ is a vector of the selected subset of features for bag j.

13. The computer readable program storage device of claim 9, the method further comprising evaluating a label prediction of a current bag by the trained failure prediction model using a maximal prediction score of all instances in flail the current bag.

* * * * *